(12) United States Patent  (10) Patent No.: US 8,435,252 B2
Smith  (45) Date of Patent: May 7, 2013

(54) WOUND CLOSURE DEVICE

(75) Inventor: Robert C. Smith, Middletown, CT (US)

(73) Assignee: Covidien LP, Mansfield, MA (US)

( * ) Notice: Subject to any disclaimer, the term of this patent is extended or adjusted under 35 U.S.C. 154(b) by 211 days.

(21) Appl. No.: 12/908,944

(22) Filed: Oct. 21, 2010

(65) Prior Publication Data

US 2011/0112553 A1  May 12, 2011

Related U.S. Application Data

(60) Provisional application No. 61/260,121, filed on Nov. 11, 2009.

(51) Int. Cl.
*A61B 17/04* (2006.01)
(52) U.S. Cl.
USPC .......................................... 606/144; 606/148
(58) Field of Classification Search .................. 606/139, 606/144–145, 147–148; 289/16–17; 112/169
See application file for complete search history.

(56) References Cited

U.S. PATENT DOCUMENTS

| | | |
|---|---|---|
| 4,733,664 A | 3/1988 | Kirsch et al. |
| 6,911,034 B2 * | 6/2005 | Nobles et al. ................. 606/144 |
| 7,160,309 B2 | 1/2007 | Voss |
| 7,235,087 B2 | 6/2007 | Modesitt et al. |
| 7,449,024 B2 | 11/2008 | Stafford |
| 2004/0097982 A1 | 5/2004 | Jugenheimer et al. |
| 2005/0043746 A1 * | 2/2005 | Pollak et al. ................. 606/144 |
| 2005/0149066 A1 * | 7/2005 | Stafford ........................ 606/144 |
| 2005/0288707 A1 | 12/2005 | De Canniere et al. |
| 2006/0030868 A1 * | 2/2006 | Bennett, III ................... 606/148 |
| 2006/0069397 A1 | 3/2006 | Nobles et al. |
| 2009/0143808 A1 | 6/2009 | Houser |

* cited by examiner

*Primary Examiner* — Corrine M McDermott
*Assistant Examiner* — Robert A Lynch

(57) ABSTRACT

A suturing device includes a housing having an elongated tubular member extending from a distal end thereof. A head assembly is disposed at a distal end of the elongated tubular member and is configured to retain a portion of a suture therein. At least one arm member is positioned about the elongated tubular member. Each arm members includes a ferrule assembly disposed at a distal end thereof. Each ferrule assembly is positioned within a recess defined within the elongated tubular member and is configured to releasably retain a ferrule therein. Each ferrule is configured to retain a portion of the suture therein. Each arm member is rotatable to thereby rotate the ferrule assembly disposed thereon between a first position and a second position. The ferrule assembly extends at least partially radially outwardly from the recess in one of the first and second positions.

20 Claims, 3 Drawing Sheets

WOUND CLOSURE DEVICE

CROSS REFERENCE TO RELATED APPLICATION

The present application claims the benefit of and priority to U.S. Provisional Application Ser. No. 61/260,121 filed on Nov. 11, 2009, the entire contents of which are incorporated herein by reference.

BACKGROUND

1. Technical Field

The present disclosure relates to a wound closure device and, more particularly, to a wound closure device for suturing an opening in tissue.

2. Background of Related Art

Puncture wounds, wounds that pierce through tissue, may result from trauma or may be intentionally created in order to provide access to a body cavity during surgical procedures. During endoscopic surgical procedures, for example, a trocar device is utilized to puncture the peritoneum to provide an access port by way of a cannula through the abdominal wall. Generally, a trocar and/or cannula is placed through the abdominal wall for introduction of surgical instrumentation which is necessary to carry out the surgical procedure. In this manner, the surgeon may introduce a surgical instrument such as a grasper, scissor, clip applier, stapler or any other surgical instrument which may be necessary during the particular surgical procedure. Once the procedure is complete, it is necessary to close the wound.

Conventional instruments for closing puncture wounds generally include a shaft that can be extended into the body through either the puncture wound itself (in the case of a puncture caused by trauma) or through a cannula (in the case of a puncture created to access a surgical site). Suture retaining needles are then deployed from the shaft into tissue. Unfortunately, the mechanisms used for deploying the needles are often cumbersome and may make the extension and/or retraction of the suturing device difficult.

SUMMARY

In accordance with the present disclosure, a suturing device is provided. The suturing device includes a housing having an elongated tubular member extending from a distal end thereof. A head assembly is disposed at a distal end of the elongated tubular member and is configured to retain a portion of a suture therein. One or more arm members are positioned about the elongated tubular member. A ferrule assembly is disposed at a distal end of each of the arm members and is positioned within a recess defined within the elongated tubular member. Each ferrule assembly is configured to releasably retain a ferrule therein. Each ferrule is configured to retain a portion of the suture therein. The arm member(s) are rotatable to rotate the ferrule assemblies disposed thereon between a first position and a second position. In one of the first and second positions, the ferrule assembly extends at least partially radially outwardly from the recess defined within the elongated tubular member.

In one embodiment, each ferrule assembly includes a ferrule holder disposed at a distal end of the arm. Each ferrule holder is configured to releasably retain a ferrule therein.

In another embodiment, a guide tube extends distally through the housing and along each of the arm members. Each guide tube is configured to allow translation of a needle therethrough. The guide tube(s) directs the needle toward the ferrule retained within the ferrule assembly.

In yet another embodiment, the needle and the ferrule are dimensioned to engage each other in a male-female friction-fit engagement.

In still yet another embodiment, the suturing device further includes a tissue clamp disposed about the elongated tubular member. The tissue clamp is configured to translate along the elongated tubular member.

In still another embodiment, the housing further includes one or more rotatable flanges extending proximally from the housing. Each rotatable flange is configured to rotate one of the ferrule assemblies between the first and second positions.

A method for suturing is also provided in accordance with the present disclosure. The method includes providing a suturing device as described above. The method further includes inserting the suturing device into an opening in tissue such that the ferrules are positioned adjacent an internal face of tissue, rotating the ferrule assemblies from the first position to the second position such that each ferrule assembly extends at least partially radially outwardly from the recess defined within the elongated tubular member, translating a needle distally through tissue and into engagement with one of the ferrules, and translating the needle proximally through tissue such that the ferrule and the portion of suture are also translated through tissue.

In one embodiment, the method further includes removing the ferrule from the needle and translating the needle distally through tissue and into engagement with another one of the ferrules. The needle, which is engaged with the ferrule, is then translated proximally through tissue such that the suture is disposed through tissue. Next, the ferrule assemblies are rotated to the first position and the suturing device is removed from the opening in tissue so that the sutures can be tied off.

In another embodiment, the tissue clamp is translated distally along the elongated tubular member to clamp tissue between the tissue clamp and ferrules. Once the tissue clamp is in position, the needle may be translated distally through tissue and into engagement with one of the ferrules.

BRIEF DESCRIPTION OF THE DRAWINGS

Various embodiments of the presently disclosed suturing instrument are described hereinbelow with references to the drawings, wherein.

DETAILED DESCRIPTION OF THE EMBODIMENTS

Figures 1, 2:
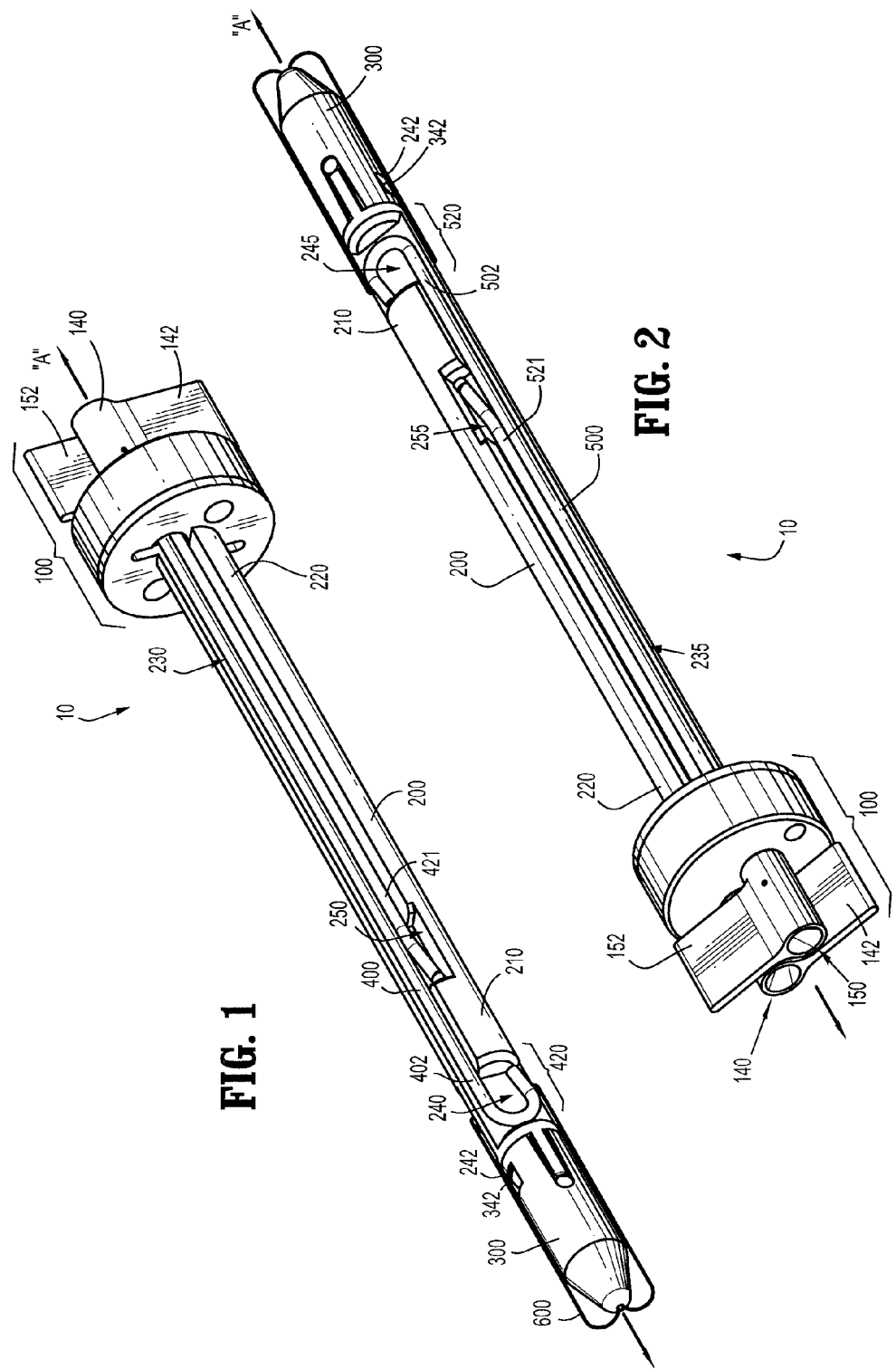
FIG. 1 is a front, perspective view of a suturing device in accordance with the present disclosure.
FIG. 2 is a rear, perspective view of the suturing device of FIG. 1.

In the figures and in the description that follows, in which like reference numerals identify similar or identical elements, the term "proximal" will refer to the end of the apparatus which is closest to the operator during use, while the term "distal" will refer to the end which is farthest from the operator, as is traditional.

Figure 4:
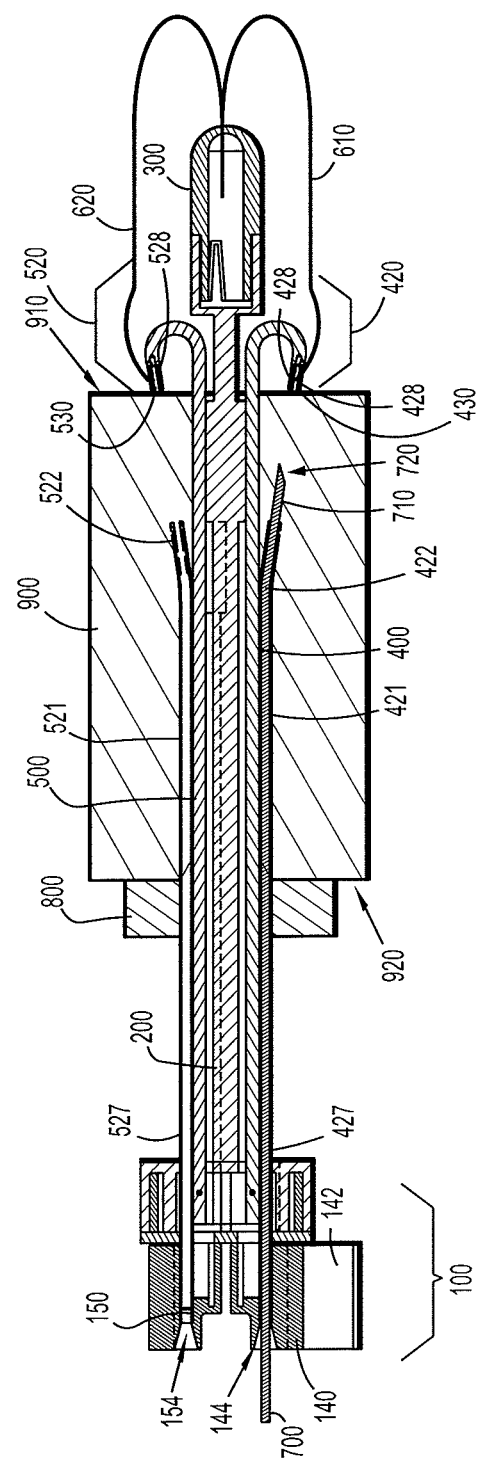
FIG. 4 is a top, cross-sectional view of the suturing instrument of FIG. 1.

Turning now to FIGS. 1-2, suturing instrument 10 defines longitudinal axis "A" and generally includes a housing 100, an elongated tubular member 200 extending distally from the housing 100, a head assembly 300 disposed at a distal end 210 of the elongated tubular member 200, and a pair of arm members 400, 500 positioned about elongated tubular member 200 and extending along elongated tubular member 200. As shown in FIGS. 1-2, two arm members 400, 500 are provided, each having a proximal end 404, 504 and a distal end 402, 502, respectively. However, it is envisioned that fewer or more arm members may be provided for use with suturing instrument 10. Arm members 400, 500 are fully disposed within elongated channels 230 and 235 defined on opposing sides of elongated tubular member 200. As will be described in greater detail below, arm members 400 and 500 are rotatable, thereby rotating ferrule assemblies 420 and 520, respectively, between a first position and a second position. Ferrule assembly 420, attached to a distal end 402 of arm 400, is rotatable from a first position in which ferrule assembly 420 is fully disposed within recess 240 defined within elongated tubular member 200 (FIG. 1) to a second position in which ferrule assembly 420 is rotated to extend radially outwardly from recess 240 of elongated tubular member 200 (FIG. 4). Similarly, ferrule assembly 520 is attached to a distal end 502 of arm member 500 and is initially disposed within recess 245 defined within elongated tubular member 200. When rotated to the second position (FIG. 4), ferrule assembly 520 extends radially outwardly from recess 245 of elongated tubular member 200.

Figure 3:
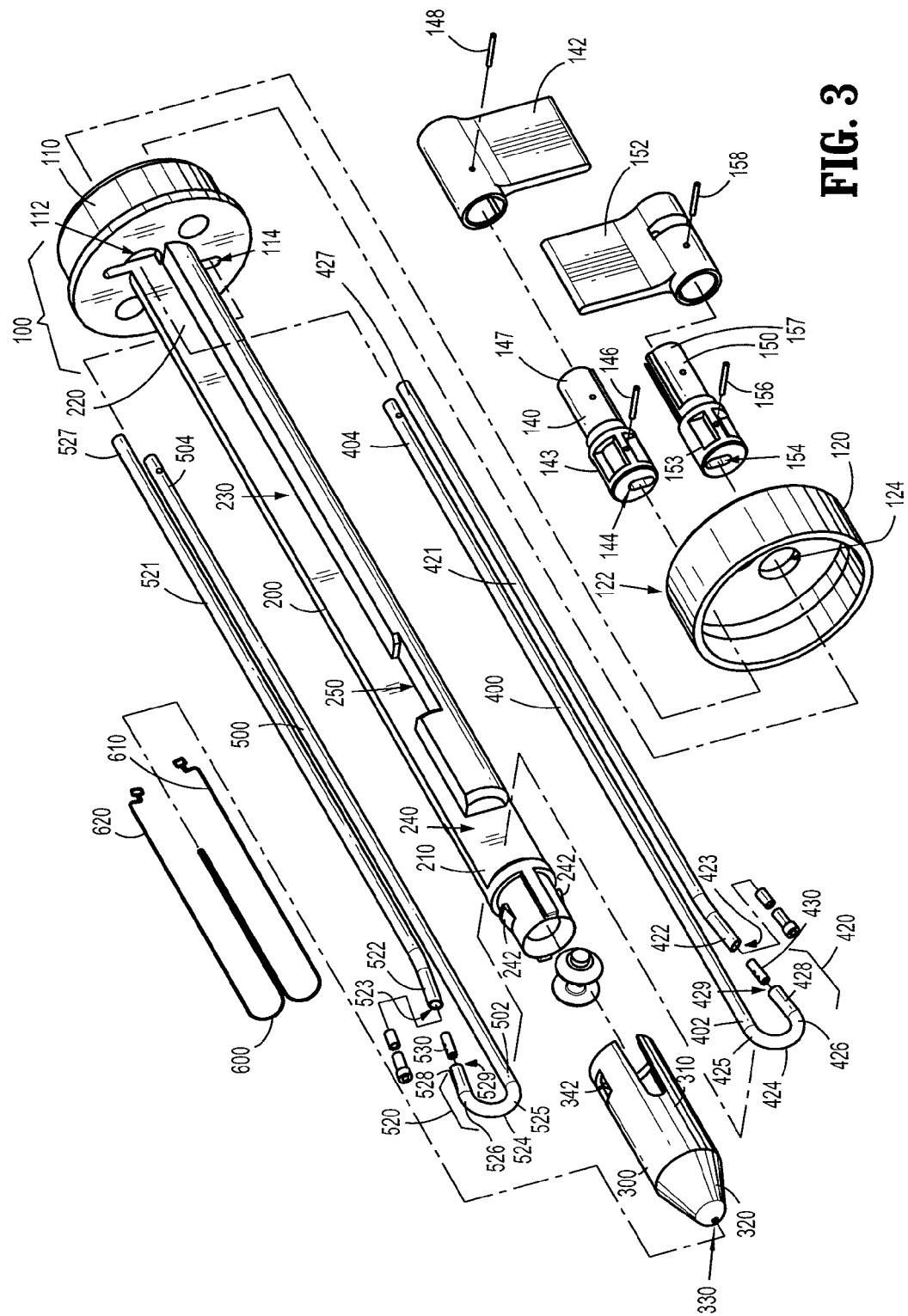
FIG. 3 is an exploded view of the suturing device of FIG. 1 with parts separated.

With reference now to FIGS. 1-3, each ferrule assembly 420, 520 includes a curved portion 424, 524 and a ferrule holder 428, 528. The curved portions 424, 524 are fixedly attached at a first end 425, 525 to the distal end 402, 502 of the corresponding arm member 400, 500 and at a second end 426, 526 to the respective ferrule holder 428, 528 of the respective ferrule assembly 420, 520. Each ferrule holder 428, 528 includes a lumen 429, 529 for releasably housing a ferrule 430, 530 therein. As can be appreciated, as arm members 400, 500 are rotated, ferrule assemblies 420, 520 are rotated between a first position, in which ferrule holders 428, 528 are fully disposed within recesses 240, 245 of elongated tubular member 200, and a second position, in which ferrule holders 428, 528 extend at least partially radially outwardly from recesses 240, 245 of elongated tubular member 200.

With continued reference to FIGS. 1-3, a guide tube 421, 521, having a respective guide lumen 423, 523 extending therethrough is positioned adjacent each of the arm members 400, 500. Guide tube 421 is positioned in a side-by-side relationship with arm member 400 such that a substantial portion of guide tube 421 and arm 400 run substantially parallel to one another. Similarly, a substantial portion of guide tube 521 runs substantially parallel to arm member 500. As will be discussed in detail below, aim member 400 and guide tube 421 are rotated simultaneously, such that guide tube 421 rotates about arm member 400. Similarly, arm member 500 and guide tube 521 are rotated simultaneous such that guide tube 521 rotates about arm member 500. Further, guide tubes 421, 521 each include a deflected distal end 422, 522. The deflected distal ends 422, 522 are initially positioned within recesses 250 and 255 of elongated tubular member 200 but are rotatable to extend radially outwardly from recesses 250 and 255 upon rotation of arm member 400, 500, respectively. As mentioned above, the rotation of arm members 400, 500 causes rotation of guide tubes 421, 521 about the respective arm member 400, 500 and also causes simultaneous rotation of ferrule assemblies 420, 520. Thus, the deflected distal ends 422, 522 of guide tubes 421, 521 are rotatable in conjunction with the rotation of ferrule assemblies 420, 520, the importance of which will be come more apparent below.

Referring now to FIG. 3, head assembly 300 includes a base portion 310 and a tip portion 320. Tip portion 320 of head assembly 300 may be generally conically shaped to facilitate the insertion of suturing instrument 10 through an opening in tissue 900 (FIG. 4) and/or may also include a blunt tip portion to help avoid damaging tissue upon insertion of instrument 10 into an opening in tissue 900 (FIG. 4). Aperture 330 is configured to releasably retain a portion of suture 600 therein. A first end 610 of suture 600 extends from aperture 330 and is attached to ferrule 430, while a second end 620 of suture 600 extends from aperture 330 and is attached to ferrule 530. Head assembly 300 may be mounted to distal end 210 of elongated tubular member 200 via adhesion, friction-fitting, snap-fitting, or the like. As shown in FIG. 3, head assembly 300 includes notches 342 for engagement with tabs 242 respectively, of elongated tubular member 200 to engage head assembly 300 thereon in a snap-fit engagement.

With continued reference to FIG. 3, housing 100 is positioned at a proximal end 220 of elongated tubular member 200 and generally includes a base 110 and a cover 120. The base 110 and cover 120 are configured to engage one another to form housing 100. Base 110 is engaged with proximal end 220 of elongated tubular member 200 and includes a pair of diametrically opposed apertures 112 and 114, respectively, extending therethrough. Cover 120 similarly includes a pair of opposed apertures 122 and 124. Upon engagement of the base 110 and cover 120 to form housing 100, apertures 112 and 114 of base 110 are aligned with apertures 122 and 124, respectively, of cover 120. A post 140 is positioned through housing 100 via apertures 112 and 122, which are of sufficient diameter to allow post 140 to be rotatable within apertures 112 and 122. A double lumen 144 is defined within distal end 143 of post 140, which extends through housing 100. Double lumen 144 is configured to engage proximal ends 404 and 427 of arm member 400 and guide tube 421, respectively therein. A pin 146 is inserted through post 140 and arm member 400, to fixedly engage arm member 400 and guide tube 421 within double lumen 144 of post 140, as shown in FIG. 3. Accordingly, the rotation of post 140 causes the like rotation of both arm member 400 and guide tube 421. A proximal end 147 of post 140 extends proximally through aperture 122 of cover 120 and is engaged via pin 148 to flange 142 such that rotation of flange 142 rotates post 140, which in turn rotates arm member 400 and guide tube 421.

A second post 150 is inserted through aperture 114 of base 110 and aperture 124 of cover 120 of housing 100. Distal end 153 of post 150 extends through housing 100 and is engaged in a fixed relationship with arm member 500 and guide tube 521 disposed through double lumen 154 and held in place via pin 156. Proximal end 157 of post 150 extends proximally from housing 100 and is engaged with flange 152 via pin 158. Much like the configuration of post 140 and flange 142, rotation of flange 152 rotates post 150, which in turn rotates arm member 500 and guide tube 521. Although not explicitly shown in the drawings, double lumens 144 and 154 of posts 140 and 150, respectively, extend proximally through posts 140 and 150, such that lumen 144 provides a passage extending from the proximal end of housing 100 to the proximal end 427 of guide tube 421 and such that lumen 154 provides a passage extending from the proximal end of housing 100 to the proximal end 527 of guide tube 521. As will become apparent below, these passages allow a user to insert a needle 700 (FIG. 4) through the proximal end of housing 100 into the guide tubes 421, 521.

As shown in FIG. 4, suturing instrument 10 may also include a tissue clamp 800. Tissue clamp 800 is disposed about elongated tubular member 200 and is axially translatable with respect to elongated tubular member 200 along longitudinal axis "A" (FIG. 1). As will become more apparent below, tissue clamp 800 is configured to translate along elongated tubular member 200 to hold tissue 900 in place during suturing. Thus, tissue clamp 800 allows suturing instrument 10 to be used for suturing tissues having varying widths. Further, tissue clamp 800 helps prevent slippage of tissue 900 during suturing, thereby helping to ensure proper placement of the sutures 600.

The operation of suturing instrument 10 will now be described with reference to FIGS. 1-4. Initially, flanges 140 and 150 are rotated to the first, or closed position, as shown in FIG. 1, such that ferrule assemblies 420, 520 are fully disposed within recesses 240, 245, respectively, and such that guide tubes 421, 521 are fully disposed within recesses 250, 255, respectively, of elongated tubular member 200. From this closed position, suturing instrument 10 may be inserted into an opening in tissue 900, lead by head assembly 300. Suturing instrument 10 is translated through the opening in tissue 900 until the ferrule holders 428, 528, and thus the ferrules 430, 530, are positioned adjacent an internal face 910 of tissue 900. Flange 142 and/or flange 152 are then rotated outwardly, to the position shown in FIG. 4 (the open position), such that ferrule assemblies 420, 520 and guide tubes 421, 521 extend radially outwardly from recesses 240, 245 and 250, 255, respectively, of elongated tubular member 200. At this point, ferrule holders 428, 528 are abutting an internal face 910 of tissue 900, as shown in FIG. 4. Tissue clamp 800 is then moved distally along elongated tubular member 200 to abut external face 920 of tissue 900, thereby holding tissue 900 in place between ferrule holders 428, 528 and tissue clamp 800.

Next, a needle 700 is inserted through aperture 144 of post 140 and into guide tube 421. Upon distal translation of needle 700, distal tip 710 of needle 700 eventually translates completely through guide tube 421, entering tissue 900. Deflected distal tip 422 of guide tube 421 guides needle 700 through tissue 900 and into ferrule holder 428. As needle 700 is urged further distally into ferrule holder 428, needle 700 surrounds ferrule 430 such that ferrule 430 is disposed through lumen 720 of needle 700. Lumen 720 may have a slightly smaller diameter than ferrule 430 such that when needle 700 is urged around ferrule 430, ferrule 430 becomes lodged within lumen 720, fixedly retaining ferrule 430 therein via a male-female friction-fit engagement. Alternatively, lumen 720 may taper proximally from distal tip 710 from a first diameter which is larger than the diameter of ferrule 430 to a second diameter which is smaller than the diameter of ferrule 430. In this configuration, further urging of needle 700 around ferrule 430 engages ferrule 430 within lumen 720 in a male-female friction-fit engagement. In another alternative embodiment, needle 700 may be solid and of a sufficiently small diameter to engage a lumen (not shown) defined in ferrule 430. In this embodiment, needle 700 may be urged into the lumen defined in ferrule 430 such that the ferrule 430 and needle 700 are engaged in a male-female friction-fit engagement.

Once ferrule 430 is fixedly engaged with needle 700, needle 700 may be translated proximally out of ferrule holder 428 and back through tissue 900. Since end 610 of suture 600 is attached to ferrule 430, a portion of suture 600 is pulled through tissue 900 along with needle 700 and ferrule 430. Upon further proximal translation, needle 700 is removed from guide tube 421 and aperture 144 of post 140. At this point, a middle portion of suture 600 is retained within aperture 330 of head assembly 300, end 610 of suture 600 extends from aperture 300 proximally through tissue 900 due to its engagement with ferrule 430, and end 620 of suture 600 remains attached to ferrule 530, disposed on an internal side 910 of tissue 900 within ferrule holder 528.

Next, needle 700, or a different needle substantially similar to needle 700, is inserted into aperture 154 of post 150 and through guide tube 521. Deflected distal end 522 of guide tube 521 directs needle 700 through tissue 900 and toward ferrule holder 528. As similarly described above, needle 700 is then advanced through ferrule holder 528 to engage ferrule 530 therein in a male-female friction-fit engagement. Needle 700 and ferrule 530 are then translated proximally back through tissue 900, as described above, such that end 620 of suture 600 is disposed through tissue 900. Needle 700 may then be removed from guide tube 521 and post 150. Once the suture ends 610 and 620 are in place, as described above, tissue clamp 800 may be translated proximally, disengaging external surface 920 of tissue 900. With needle 700 removed from suturing instrument 10 and tissue clamp 800 released from tissue 900, flanges 142, 152 may be rotated to the closed position such that ferrule assemblies 420 and 520 and guide tubes 421 and 521 are rotated back to the closed position in which ferrule assemblies 420 and 520 are fully disposed within recesses 240 and 245, respectively, of elongated tubular member 200 and wherein deflected distal ends 422, 522 of guide tubes 421, 521, respectively, are fully disposed within recesses 250 and 255, respectively, of elongated tubular member 200.

At this point, the middle portion of suture 600 is retained within aperture 330 of head assembly 300, on an internal side 910 of tissue 900 while ends 610 and 620 of suture 600 extend proximally through tissue 900. From here, instrument 10 may be withdrawn from the opening in tissue 900. As instrument 10 is removed from the opening in tissue 900, the portion of suture 600 is released from aperture 330, such that the portion of suture 600 remains on an internal side 910 of tissue 900. Once instrument 10 is removed, ends 610 and 620, disposed on the external side 920 of tissue 900, may be tied together to thereby close the opening in tissue 900.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. A suturing device, the suturing device comprising:
a housing having an elongated tubular member extending from a distal end thereof, the elongated tubular member defining a first longitudinal axis;
a head assembly disposed at a distal end of the elongated tubular member and configured to retain a portion of a suture therein;
at least one arm member positioned about the elongated tubular member, the at least one arm member including a ferrule assembly disposed at a distal end thereof, the ferrule assembly positioned within a first recess defined within the elongated tubular member and configured to releasably retain a ferrule therein, the ferrule configured to retain a portion of the suture therein; and
at least one guide tube positioned about the elongated tubular member and including a distal end positioned within a second recess defined within the elongated tubular member, the guide tube configured for translation of a needle therethrough,
wherein the at least one arm member and the at least one guide tube are configured to rotate about a second longitudinal axis that is substantially parallel to the first longitudinal axis between a first position, wherein the ferrule assembly is disposed within the first recess and the distal end of the guide tube is disposed within the second recess, and a second position, wherein the ferrule assembly extends at least partially radially outwardly from the first recess and the distal end of the guide tube extends at least partially radially outwardly from the second recess to direct the needle toward the ferrule retained within the ferrule assembly.

2. The suturing device according to claim 1, wherein each ferrule assembly includes a ferrule holder disposed at a distal end of the arm, the ferrule holder configured to releasably retain the ferrule therein.

3. The suturing device according to claim 1, wherein the distal end of the guide tube defines a deflected configuration configured to direct the needle toward the ferrule retained within the ferrule assembly in the second position.

4. The suturing device according to claim 1, wherein the needle and the ferrule are dimensioned to engage each other in a male-female friction-fit engagement.

5. The suturing device according to claim 1, further including a tissue clamp disposed about the elongated tubular member and configured for translation along the elongated tubular member.

6. The suturing device according to claim 1, wherein the housing further includes at least one rotatable flange extending proximally therefrom, each rotatable flange configured to rotate the at least one arm member and the at least one guide tube between the first and second positions.

7. The suturing device according to claim 1, wherein the at least one arm member and the at least one guide tube are configured to rotate simultaneously and in conjunction with one another between the first and second positions.

8. A method for suturing, the method comprising the steps of:
providing a suturing device including:
a housing having an elongated tubular member extending from a distal end thereof, the elongated tubular member defining a first longitudinal axis;
a head assembly disposed at a distal end of the elongated tubular member, the head assembly retaining a portion of a suture therein;
at least one arm member positioned about the elongated tubular member, the at least one arm members including a ferrule assembly disposed at a distal end thereof, the ferrule assembly releasably retaining a ferrule therein, the ferrule retaining a first portion of the suture therein;
at least one guide tube positioned about the elongated tubular member, the guide tube defining a distal end;
inserting the suturing device into an opening in tissue such that the ferrule is positioned adjacent an internal face of tissue;
rotating the at least one arm member and the at least one guide tube about a second longitudinal axis that is substantially parallel to the first longitudinal axis from a first position to a second position such that the ferrule assembly and the distal end of the guide tube extend at least partially radially outwardly from the elongated tubular member;
translating a needle distally through the guide tube, tissue, and into engagement with ferrule; and
translating the needle having the ferrule in engagement therewith proximally through tissue and the guide tube to withdraw the needle from the guide tube and such that the first portion of the suture is disposed through tissue.

9. The method according to claim 8, further comprising the steps of:
removing the ferrule from the needle;
translating the needle distally through a second guide tube, tissue, and into engagement with the ferrule retained within the ferrule assembly of a second arm member;
translating the needle having the ferrule in engagement therewith proximally through tissue and the second guide tube to withdraw the needle from the second guide tube and such that a second portion of the suture is disposed through tissue;
rotating the arm members and guide tubes to the first position;
removing the suturing device from the opening in tissue; and
tying off the first and second portions of the suture.

10. The method according to claim 8, wherein the ferrule assembly includes a ferrule holder disposed at a distal end of the arm, the ferrule holder configured to releasably retain the ferrule therein.

11. The method according to claim 8, wherein the distal end of the guide tube defines a deflected configuration configured to direct the needle toward the ferrule retained within the ferrule assembly in the second position.

12. The method according to claim 8, wherein the needle and the ferrule are dimensioned to engage each other in a male-female friction-fit engagement.

13. The method according to claim 8, further including a tissue clamp disposed about the elongated tubular member and configured for translation along the elongated tubular member.

14. The method for suturing according to claim 13, further including the step of translating the tissue clamp distally along the elongated tubular member to clamp tissue between the tissue clamp and the ferrule before translating the needle distally through tissue and into engagement with the ferrule.

15. The method according to claim 8, wherein rotation of the at least one arm member and the at least one guide tube from the first position to the second position are effected simultaneously and in conjunction with on another.

16. A suturing device, comprising:
an elongated tubular member defining a first longitudinal axis;
at least one arm member extending along the elongated tubular member, the at least one arm member including a ferrule assembly disposed at a distal end thereof, the ferrule assembly configured to releasably retain a ferrule therein;
at least one guide tube extending along the elongated tubular member and defining a distal end, the at least one guide tube configured for receipt of a needle therethrough and to direct the needle toward the ferrule retained within the ferrule assembly; and
an actuator disposed at a proximal end of the elongated tubular member and coupled to both the at least one arm and the at least one guide tube, the actuator selectively actuatable to rotate the at least one arm and the at least one guide tube about a second longitudinal axis that is substantially parallel to the first longitudinal axis from a first position, wherein the ferrule assembly and the distal end of the at least one guide tube are disposed within the outer periphery of the elongated tubular member, and a second position, wherein the ferrule assembly and the distal end of the at least one guide tube extend at least partially outwardly from the outer periphery of the elongated tubular member.

17. The suturing device according to claim 16, wherein the actuator includes a rotatable flange configured to rotate about the longitudinal axis between an un-actuated position and an actuated position for rotating the at least one arm member and at least one guide tube between the first and second positions.

18. The suturing device according to claim 16, wherein each ferrule assembly includes a ferrule holder configured to releasably retain the ferrule therein.

19. The suturing device according to claim 16, wherein the distal end of the at last one guide tube defines a deflected configuration configured to direct the needle toward the ferrule retained within the ferrule assembly.

20. The suturing device according to claim 16, wherein the actuator is configured to simultaneously rotate the at least one arm and the at least one guide tube in conjunction with one another between the first position and second positions.

* * * * *